(12) United States Patent
Fenchel

(10) Patent No.: US 8,552,387 B2
(45) Date of Patent: Oct. 8, 2013

(54) METHOD FOR DETERMINING RADIATION ATTENUATION BY AN EXAMINATION OBJECT IN A POSITRON EMISSION TOMOGRAPHY SCANNER

(75) Inventor: Matthias Fenchel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 239 days.

(21) Appl. No.: 13/158,727

(22) Filed: Jun. 13, 2011

(65) Prior Publication Data

US 2011/0303835 A1    Dec. 15, 2011

(30) Foreign Application Priority Data

Jun. 15, 2010  (DE) .......................... 10 2010 023 847

(51) Int. Cl.
 *G01T 1/166* (2006.01)
(52) U.S. Cl.
 USPC ................................................. 250/363.04
(58) Field of Classification Search
 USPC ....................................... 250/363.03, 363.04
 See application file for complete search history.

(56) References Cited

U.S. PATENT DOCUMENTS

2008/0135769 A1   6/2008   Rosen

OTHER PUBLICATIONS

Grady et al.; Random walks for Image segmentation Grady et al.; IEEE TRansactions on Pattern Analysis and Machine Intelligence 28(11) (2006) 1768-1783; Others; 2006.

J. Nuyts et al: "Simultaneous maximum a posteriori reconstruction of attenuation and activity distributions from emmission sinograms", IEEE Trans. Med. Imag., vol. 18, No. 5, May 1999, pp. 393-403; Others; 1999.
Andrei V. Bronnikov: "Reconstruction of Attenuation Map Using Discrete Consistency Conditions", IEEE Transactions on Medical Imaging, vol. 19, No. 5, May 2000, p. 451-462; Others; 2000.
Fabiana Crepaldi et al.: "Activity and Attenuation Reconstruction of Positron Emission Tomography Using Emission Data Only Via Maximum Likelihood and Iterative Data Refinement", IEEE Transactions on Nuclear Science, vol. 54, No. 1, Feb. 2007,; Others; 2007.
Yuri Boykov et al.: "Interactive Organ Segmentation Using Graph Cuts" Medical Image Computing and Computer-Assisted Intervention, MICCAI 2000, p. 276-286; Others; 2000.
Andre Salomon et al.: "Simultaneous Reconstruction of Activity and Attenuation in Multi-Modal ToF-PET", In: Proceedings of the 10th Fully 3D Meeting and 2nd HPIR Workshop. 2009, p. 339-342; Others; 2009.

*Primary Examiner* — Mark R Gaworecki
(74) *Attorney, Agent, or Firm* — Harness, Dickey & Pierce, P.L.C.

(57) ABSTRACT

In an embodiment, an initial segmentation of an examination object is fixed, wherein an attenuation coefficient is assigned to each segment of the segmentation. Raw radiation data about the examination object arranged in the positron emission tomography scanner is acquired, and a correction factor is determined for each pixel with the aid of an optimization method, in which the probability of the acquired raw radiation data is maximized taking into account the segmentation and the attenuation coefficients assigned to the segments. A statistical parameter of the correction factors is determined for each segment and the segmentation is corrected by subdividing a segment as a function of the statistical parameter determined for the segment. A segment correction factor is determined for each segment from the correction factors assigned to the segment and the attenuation coefficients assigned to the segments are corrected as a function of the segment correction factors.

17 Claims, 4 Drawing Sheets

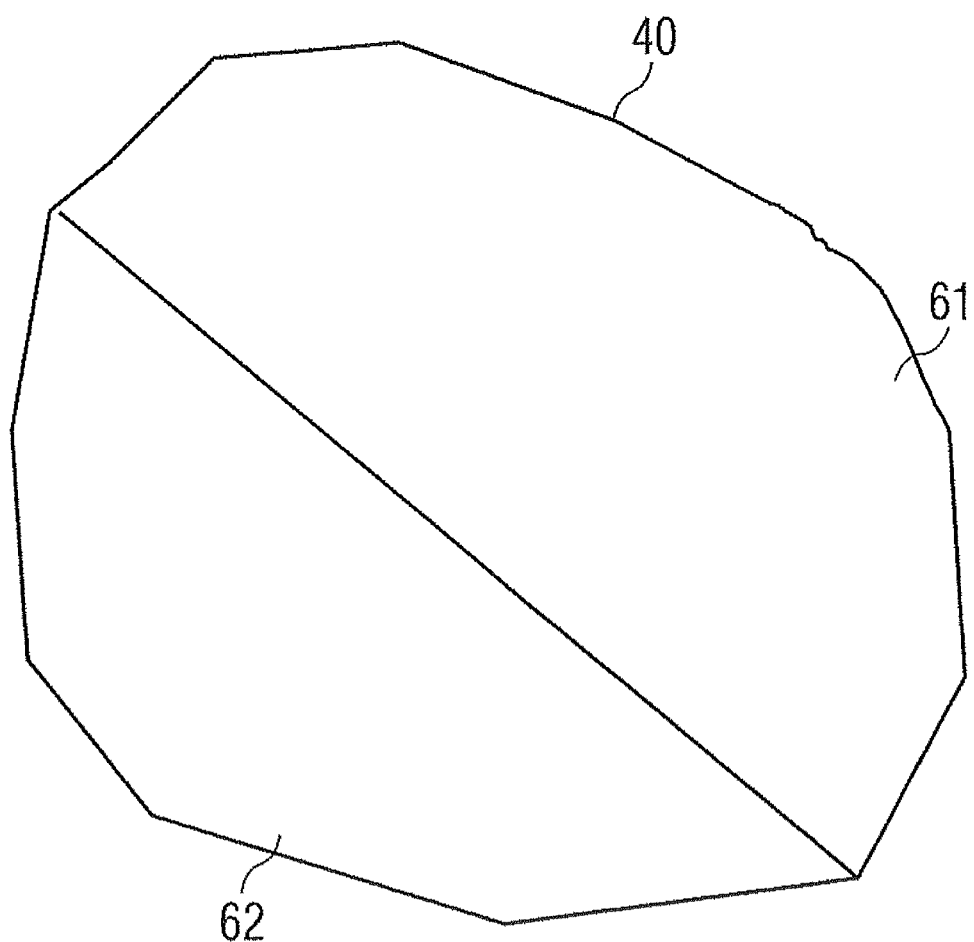

METHOD FOR DETERMINING RADIATION ATTENUATION BY AN EXAMINATION OBJECT IN A POSITRON EMISSION TOMOGRAPHY SCANNER

PRIORITY STATEMENT

The present application hereby claims priority under 35 U.S.C. §119 on German patent application number DE 10 2010 023 847.3 filed Jun. 15, 2010, the entire contents of which are hereby incorporated herein by reference.

FIELD

At least one embodiment of the present invention generally relates to a method for determining radiation attenuation by an examination object in a positron emission tomography scanner and, more particularly, at least one embodiment relates to a method for determining radiation attenuation on the basis of a magnetic resonance recording and a positron emission tomography recording.

BACKGROUND

One of the most difficult objects in positron emission tomography systems (PET-systems) includes determining the attenuation correction as precisely as possible. Since the gamma quanta, which are generated in the examination object by an interaction between a positron and an electron, pass through the entire region within the detector ring before they are counted by the detector ring, they are attenuated by objects, more particularly by the examination object itself, within the examination region, the so-called field of view (FoV). Hence this attenuation must be corrected in order to obtain images that can be used in a clinical context.

By way of example, this radiation attenuation within an examination object, for example within a human body, can be determined on the basis of a magnetic resonance image. However, a problem here is that the magnetic resonance image or the magnetic resonance signals only weakly correlate with the electron density or the associated linear attenuation coefficients (LAC) of human tissues at the annihilation radiation energy of 511 keV.

In the prior art, as disclosed in, for example, US 2008/135769, it is conventional to produce a magnetic-resonance-based determination of a so-called PET attenuation map by segmenting the magnetic resonance image into different tissue types and assigning appropriate LAC values. Other approaches for a magnetic-resonance-based attenuation correction use a model or a reference image with known attenuation from e.g. a corresponding computed tomography recording or body contours, which are derived from an optical 3D scan. The magnetic resonance image is then combined with the model or the reference image with the known attenuation, and the actual attenuation map is obtained from the combined information.

In further methods, iterative estimation methods are used to obtain simultaneously emission images and attenuation maps from the raw PET data. In the process, use can be made for example of so-called maximum likelihood expectation maximization (MLEM) algorithms, as described in, for example, the following publications:

1) IEEE Trans. Med. Imag., volume 18, p. 393-03, 1999. Simultaneous maximum a posteriori reconstruction of attenuation and activity distributions from emission sinograms, J. Nuyts, S. S. Dupont, R. Benninck, L. Mortelmans, and P. Suetens 2) IEEE Transactions on Medical Imaging, volume 19, number 5, May 2000 451, Reconstructions of Attenuation Map Using Discrete Consistency Conditions, Andrei V. Bronnikov 3) IEEE Transactions of Nuclear Science, volume 54, number 1, February 2007, Activity and Attenuation Reconstruction for Positron Emission Tomography Using Emission Data Only Via Maximum Likelihood and Iterative Data Refinement, Fabiana Crepaldi and Alvaro R. De Pierro These algorithms usually converge to a local maximum and therefore have to be bounded to achieve the desired solution.

The prior art, as disclosed by Andre Salomon et al. in "Simultaneous Reconstruction of Activity and Attenuation in Multi-Modal ToF-PET" ($10^{th}$ International Meeting on Fully Three-Dimensional Image Reconstruction in Radiology and Nuclear Medicine, pages 339-344), combines a segmentation and a simultaneous reconstruction of the radiation attenuation and the emission image. In the process, the radiation attenuation is not calculated for every pixel; rather, a pre-segmentation of an image on the basis of e.g. a computed tomography image or a magnetic resonance image is used to subdivide the image into segments, and each segment is assigned a linear attenuation coefficient (LAC value) by maximizing the probability of the measured data during the given segmentation and the LAC values assigned to each segment.

In the process, correction factors are calculated and back-projected for the lines of response in order to maximize the probability for each segment in an iterative fashion. Compared to methods based only on a segmentation and assignment of linear attenuation coefficients, this method is able to adapt linear attenuation coefficients individually for each segment rather than basing them on values that, for example, were statistically averaged over a plurality of measurements on different patients. Furthermore, this method makes it possible to determine an attenuation resulting from bones; usually, this is almost impossible in the case of correction methods only based on a magnetic-resonance-based attenuation.

SUMMARY

However, the inventors have discovered that, particularly if this method is used in conjunction with a hybrid magnetic resonance-positron emission tomography system (hybrid MR-PET system), the segmentation into different segments on the basis of the magnetic resonance image does not necessarily lead to segments with more or less identical attenuation but follows the contrast of the intensities given by the magnetic resonance image acquisition, which are independent of the radiation densities. Moreover, signal variations, which may for example be caused by inhomogeneities, may cause different tissue types to appear to have the same intensity or identical tissue types to appear to have different intensities.

Even in the case of complicated methods, such as e.g. the model-based segmentations, the segments can contain pixels from very different tissue-attenuation classes as a result of over-segmentation or under-segmentation. This can be expected particularly in regions that contain both air and bone because the grayscale-value intensities thereof are very similar in conventional magnetic resonance recording protocols. FIG. 3B shows an example of under-segmentation on the basis of the magnetic resonance recording shown in FIG. 3A.

In at least one embodiment of the present invention, an improved method is provided for determining radiation attenuation by an examination object in a positron emission tomography scanner.

According to at least one embodiment of the present invention, a method is disclosed for determining radiation attenuation by an examination object in a positron emission tomography scanner. Further, in at least one embodiment, a positron emission tomography system is disclosed and/or a computer program product is disclosed; and/or an electronically readable data medium is disclosed. The dependent claims define preferred and advantageous embodiments of the invention.

According to at least one embodiment of the present invention, provision is made for a method for determining radiation attenuation by an examination object, for example a patient, in a positron emission tomography scanner. An initial segmentation of the examination object is fixed in the method. A mean attenuation coefficient is assigned to each segment of the segmentation and each segment comprises a plurality of pixels of the examination object. By way of example, this initial segmentation can, as described above, be fixed on the basis of a magnetic resonance image, recorded of the examination object and segmented automatically. Furthermore, raw radiation data about the examination object, which has a positron emission source, is automatically acquired with the aid of the positron emission tomography scanner.

A correction factor is determined for each pixel in the segment with the aid of an optimization method, in which a probability of the acquired raw radiation data is optimized taking into account the segmentation and the attenuation coefficients assigned to the segments. This correction factor is calculated for each pixel by back-projection and describes the deviation of the attenuation coefficient of the pixel from the mean attenuation coefficient of the segment.

By way of example, the aforementioned MLEM method can be used as the optimization method, in which the correction factor is calculated for each pixel by back-projection of the deviation as per MLEM between the expected data and the measured data. Respectively one statistical parameter of the correction factors is then automatically determined for each segment, wherein the correction factors that are assigned to the pixels of the respective segment are used in the statistical parameters of a segment. The segmentation can then be corrected automatically as a function of the statistical parameter determined for the segment, for example by subdividing the segment if the statistical parameter exceeds a certain threshold.

A new mean attenuation coefficient is then automatically determined for each segment from the mean attenuation coefficient and the correction factors that are assigned to the respective segment. Hence, starting from the initial segmentation generated on the basis of e.g. magnetic resonance data, the segmentation is automatically corrected on the basis of the raw radiation data acquired by the positron emission tomography scanner and the value of the linear attenuation coefficients is improved. By way of example, this can correct an under-segmentation of the initial segmentation.

According to one embodiment, the automatic correction of the segmentation furthermore comprises a merging of neighboring segments as a function of the attenuation coefficients and correction factors assigned to the neighboring segments. This additionally allows an automatic correction of an initial over-segmentation.

According to one embodiment, the attenuation coefficient for each segment of the initial segmentation is assigned as a function of a predetermined model. By way of example, the predetermined model can comprise information relating to anatomical arrangements. This affords the possibility of, in the initial segmentation, assigning the attenuation coefficient for each segment not only as a function of the intensity value of the pixels in the segment, but additionally as a function of the position of the segment within the examination object. The quality of the attenuation coefficients of the initial segmentation can be improved as a result of this.

According to a further embodiment, the statistical parameter is determined for each segment via the correction factors by determining a variance of the correction factors of the corresponding segment. The greater the variance of the correction factors for a segment is, the more inhomogeneous the attenuation values are within the segment. Accordingly, the variance can easily be used to determine whether a segment should be further subdivided or whether the attenuation values within the segment are sufficiently homogeneous such that no further subdivision of the segment is necessary.

According to a further embodiment, a segment to be subdivided is subdivided by applying a random walker segmentation method (Leo Grady: Random Walks for Image Segmentation. IEEE Trans. Pattern Anal. Mach. Intell. 28(11): 1768-1783 (2006), the entire contents of which is hereby incorporated herein by reference). By way of example, a pixel of the segment with the maximal correction factor and a pixel of the segment with the minimal correction factor can be used as seed points for the segmentation method. Starting from these two seed points, the segment can be subdivided in a simple and reliable fashion with the aid of the random walker segmentation method. Alternatively, use can be made of any other segmentation method, such as, for example, a graph-cut segmentation method.

According to a further embodiment, the method can be carried out a number of times in an iterative fashion. To this end, starting with the step of automatically determining the correction factors for each pixel with the aid of the optimization method, said step and all subsequent steps are carried out iteratively. However, the raw radiation data from the examination object arranged in the positron emission tomography scanner only needs to be acquired once, and the acquired raw radiation data is used unmodified in the various iteration run-throughs. Since the segmentation is automatically corrected in each iteration run-through, the segmentation is increasingly improved automatically when the method is carried out iteratively. By way of example, the method can be aborted if the segmentation was not modified, or only modified slightly, during an iteration step or if the correction factors of all pixels or of a predetermined portion of the pixels remain below a predetermined threshold.

According to at least one embodiment of the present invention, provision is furthermore made for a positron emission tomography system. The positron emission tomography system comprises a positron emission tomography scanner with a positron emission detector for detecting radiation emitted by an examination object, which is arranged in the positron emission tomography scanner. The positron emission tomography system furthermore comprises a control unit for actuating the positron emission detector and for receiving raw radiation data from the positron emission detector.

Furthermore, the positron emission tomography system comprises an image-computer unit for reconstructing image data from the acquired raw radiation data. The positron emission tomography system is embodied such that it fixes an initial segmentation of the examination object, for example by acquiring and automatically segmenting magnetic resonance imaging recordings or computed tomography recordings. Each segment in the segmentation comprises a plurality of pixels of the examination object, and an attenuation coefficient is assigned to each segment. By way of example, the attenuation coefficients can be assigned on the basis of the intensity values in the tomographic recording or on the basis of a model or on the basis of a mixture thereof. Furthermore, the positron emission tomography system is embodied to determine a correction factor for each pixel with the aid of an optimization method in order to improve the attenuation coefficients of every pixel.

By way of example, the above-described maximum likelihood expectation maximization (MLEM) method can be used as an optimization method. In the optimization method, a probability of the acquired raw radiation data is calculated taking into account the segmentation and the attenuation coefficients assigned to the segments, and a correction factor for each pixel is determined by maximizing this probability over a back-projection (as described in the cited document "Simultaneous Reconstruction of Activity and Attenuation in Multi-Modal ToF-PET", the entire contents of which is hereby incorporated herein by reference). In, addition to the cited document, the positron emission tomography system determines a statistical parameter of the correction factors for each segment on the basis of the segmentation.

The statistical parameter of a segment is determined by the correction factors, which are assigned to the pixels of the segment. The segmentation is automatically corrected by subdividing the segment as a function of the statistical parameter that was determined for the segment. By way of example, the statistical parameter may constitute a variance of the correction factors and the segment is subdivided if the variance exceeds a threshold. If the variance does not exceed the threshold, the segment is not subdivided. Furthermore, the positron emission tomography system is embodied to determine for each segment a segment correction factor for the segment, from the correction factors that are assigned to the respective segment. Finally, the attenuation coefficient, which is assigned to the segment, is automatically corrected for each segment as a function of the segment correction factor. Hence, the positron emission tomography system is suitable for carrying out at least one embodiment of the above-described method and therefore likewise comprises at least one of the above-described advantages.

Moreover, at least one embodiment of the present invention comprises a computer program product, more particularly software, which can be loaded into a storage medium of a programmable control unit of a positron emission tomography system. Program segments of this computer program product can be used to execute all the above-described embodiments of the method according to at least one embodiment of the invention when the computer program product is executed in the positron emission tomography system.

Finally, at least one embodiment of the present invention provides an electronically readable data medium, such as a CD or a DVD, on which electronically readable control information, more particularly software, is stored. If this control information is read from the data medium and stored in a positron emission tomography system, the positron emission tomography system can carry out all inventive embodiments of the above-described method.

BRIEF DESCRIPTION OF THE DRAWINGS

The present invention will be explained below on the basis of example embodiments and with reference to the drawings.

FIG. 6 shows the segment from FIG. 5 after the segmentation using the random walker algorithm.

DETAILED DESCRIPTION OF THE EXAMPLE EMBODIMENTS

Figure 1:
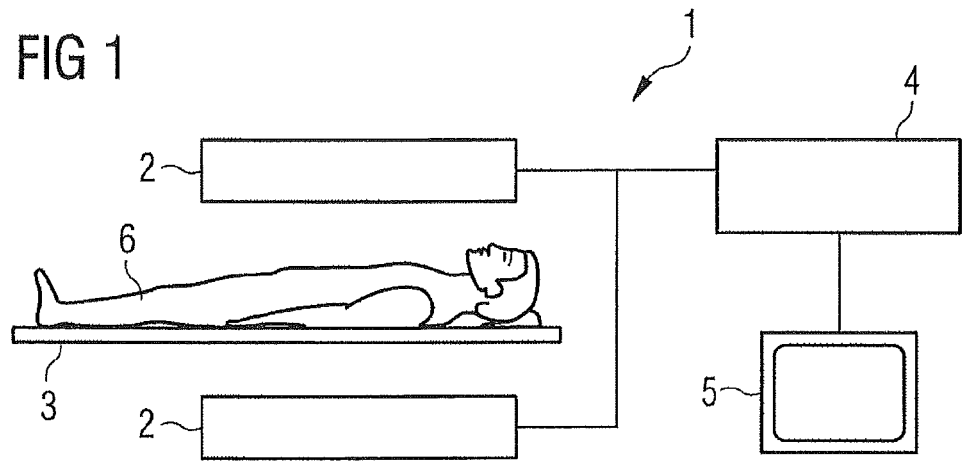
FIG. 1 schematically shows a positron emission tomography system according to an embodiment of the present invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a magnetic resonance-positron emission tomography system (MR-PET system) 1. The MR-PET system 1 comprises a tomography scanner 2, an examination table 3, a control unit 4, and an image-computer unit 5. The tomography scanner 2 has a tubular shape and is illustrated in FIG. 1 in a sectional view along the longitudinal axis of the tomography scanner 2. The tomography scanner 2 comprises all devices that are required for acquiring magnetic resonance recordings and positron emission tomography recordings. For reasons of clarity, these further devices of the tomography scanner 2 have not been illustrated in FIG. 1.

Embodiments of the present invention do not necessarily require the system 1 to be a hybrid system, which is suitable for generating magnetic resonance recordings and positron emission tomography recordings, but this is advantageous because in this case, as described below, an initial segmentation can be generated with the aid of magnetic resonance recordings and this initial segmentation can be improved with the aid of a positron emission tomography recording in order to generate an attenuation map that is as precise as possible so as to generate high-quality positron emission tomography recordings. Alternatively, the system 1 can also be a pure positron emission tomography system (PET system) and the initial segmentation can be provided in a different suitable fashion, for example from a separate CT scanner or from a separate magnetic resonance system or with the aid of anatomical models.

The examination table 3 is arranged in the interior of the tubular tomography scanner 2. The control unit 4 is coupled to the tomography scanner 2 and is able in a suitable fashion to actuate the devices (not shown here) for acquiring positron emission tomography recordings and magnetic resonance recordings, which devices are in the tomography scanner 2. A person skilled in the art is aware of this and so this will not be explained in any more detail. The image-computer unit 5 is coupled to the control unit 4 and is able to actuate the control unit 4 such that the control unit 4 provides raw data about a patient 6 arranged on the examination table 3, selectively with the aid of a magnetic resonance recording method or a positron emission tomography recording method.

The raw data provided by the control unit 4 is then processed in the image-calculation unit 5 in order to provide corresponding magnetic resonance recordings or positron emission tomography recordings for a user or medical practitioner of the MR-PET system. A person skilled in the art knows how image data corresponding to the raw data from the control unit 4 is generated in the image-calculation unit 5, and so this will not be described in any more detail.

In order to generate attenuation-corrected positron emission tomography images from the raw positron emission tomography data, information relating to a spatially dependent attenuation of the examination region is necessary for an attenuation correction. This spatially dependent attenuation is also referred to as an attenuation map or µ-map. The image data from the positron emission tomography image represents spatially dependent intensity values, which represent the spatially dependent radiation activity of the examination region. This spatially dependent radiation activity is also referred to as emission image or activity map.

Figure 2:
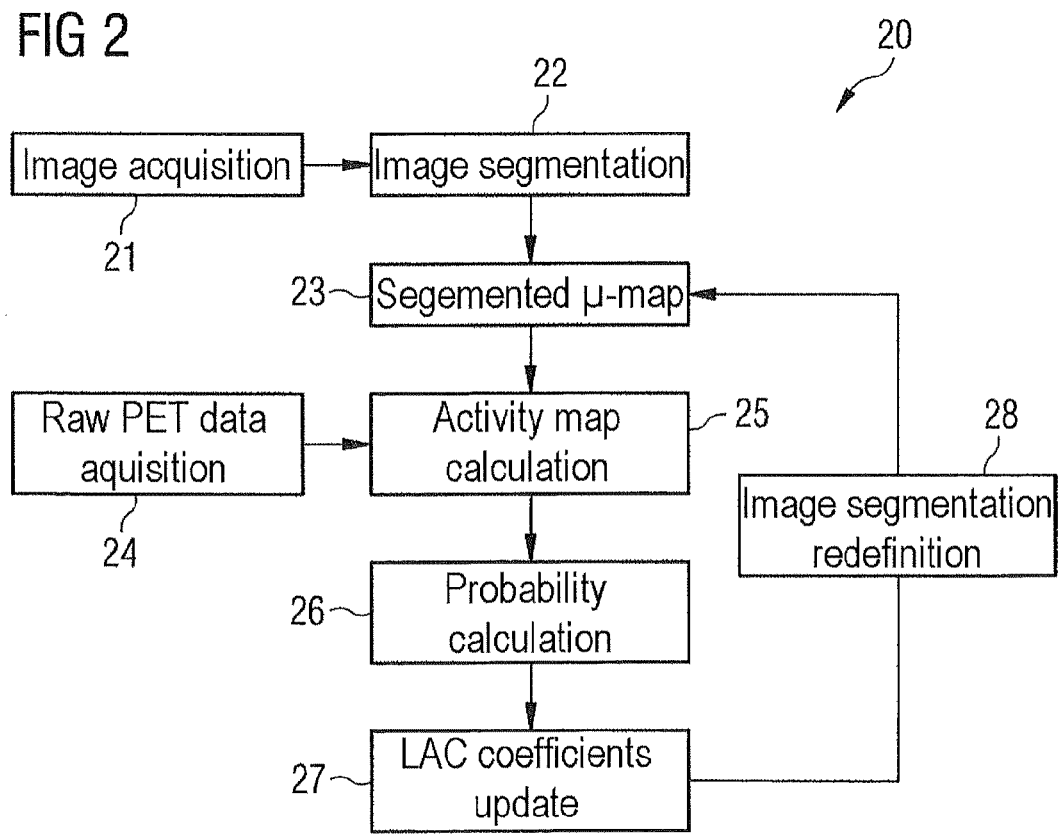
FIG. 2 shows a flowchart of an embodiment of the method according to the invention.

With reference to FIG. 2, a method 20 is described below in which a precise µ-map is generated on the basis of a rough, i.e. relatively imprecise, µ-map. In the method 20, a tomographic image of the examination object 6 is first of all acquired in step 21. By way of example, in the case of an MR-PET system, this acquisition may comprise an acquisition of a magnetic resonance recording. Alternatively, this image acquisition may, for example, also comprise a computed tomography recording acquisition or the like.

Figure 3A:
FIG. 3A shows a tomographic recording, which can be used to generate an initial segmentation.
Figure 3B:
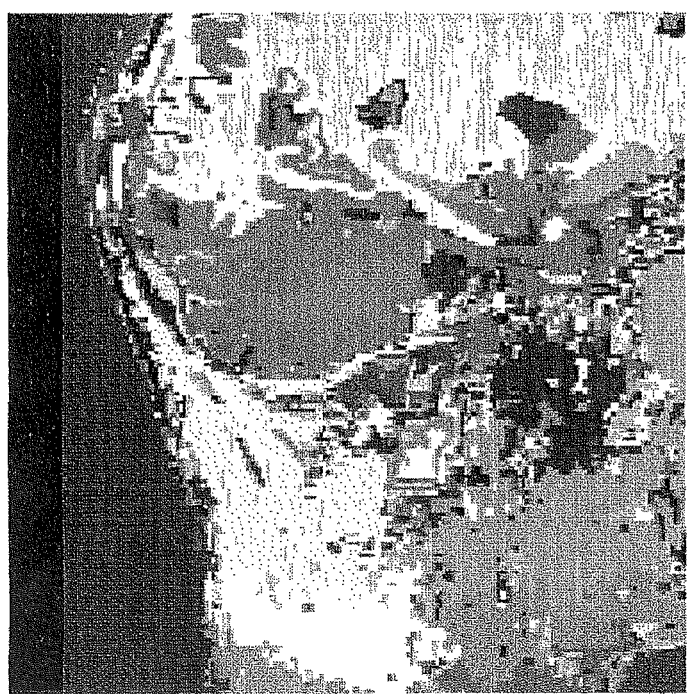
FIG. 3B shows an initial segmentation that was generated from the tomographic recording shown in FIG. 3A.

FIG. 3A shows, in an example fashion, a magnetic resonance recording that was acquired in step 21. This recording is segmented in step 22. By way of example, this segmentation can be based on a grayscale-value analysis of the acquired image. FIG. 3B shows, in an example fashion, a segmentation of the image from FIG. 3A. Related pixels with a similar grayscale value correspond to one segment in the segmentation.

FIG. 3B shows that this segmentation is comparatively rough and subdivides the image as per the contrasts (relaxation times, proton densities) given by the MRI scan, as result of which regions with different radiation attenuation occur in one segment. Radiation attenuation in the form of an attenuation coefficient is assigned to each segment in step 23 and hence a µ-map is generated, wherein each segment has precisely one value (attenuation coefficient) for the radiation attenuation. The µ-map formed thus is also referred to as a segmented µ-map.

In step 24, raw positron emission tomography data is acquired for the same examination region as for which the segmentation was generated in step 22. A positron emission tomography recording, a so-called emission image, is calculated in step 25 on the basis of the acquired raw PET data and the segmented µ-map. The correction factors for the attenuation distribution are calculated in step 26 on the basis of the calculated emission image, the segmented µ-map, and a maximum likelihood expectation maximization (MLEM) algorithm, as described in the publication by Salomon et al. (in particular, see equations (1)-(3) in section II.B of the publication by Salomon et al. mentioned above, the entire contents of which are hereby incorporated herein by reference). The attenuation coefficients assigned to the segments are corrected in step 27 on the basis of the correction factors for the attenuation distribution, as described in equation (4) by Salomon et al. Then the image segmentation is redefined in step 28 as described below.

In order to redefine the segmentation (step 28), the correction factors for each pixel are statistically analyzed for each pixel within each segment. If the total variance of the correction factors within a segment exceeds a predetermined threshold then this segment is segmented further in order to subdivide the segment into smaller parts with a lower variance. By way of example, this segmentation can be carried out using a random walker algorithm, as described by, for example, Leo Grady in "Random Walks for Image Segmentation" IEEE Transactions on Pattern Analysis and Machine Intelligence p. 1768-1783, November 2006, the entire contents of which are hereby incorporated herein by reference.

Figure 4:
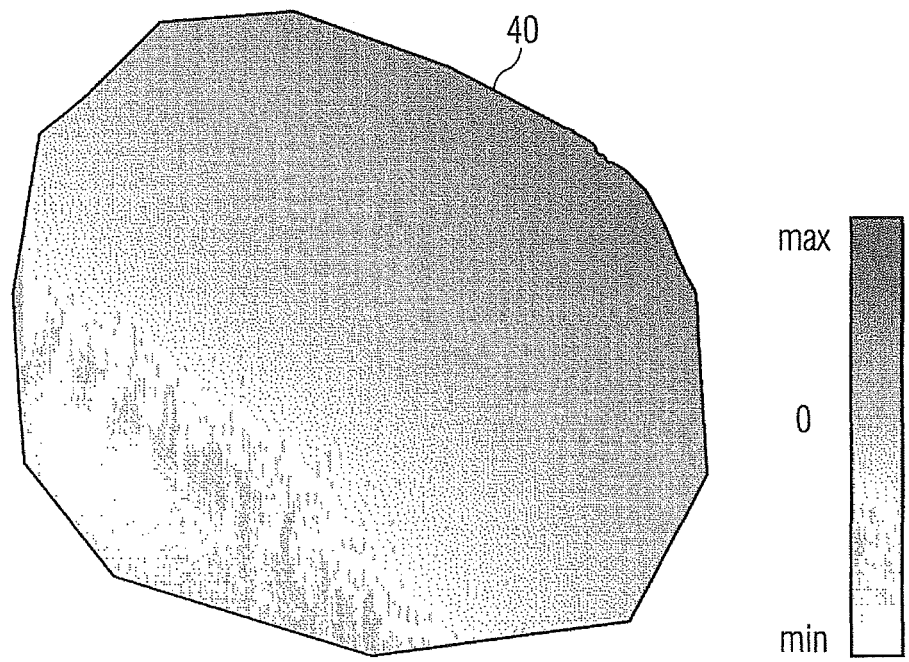
FIG. 4 shows an enlarged illustration of a segment of the segmentation illustrated in FIG. 3B.
Figure 5:
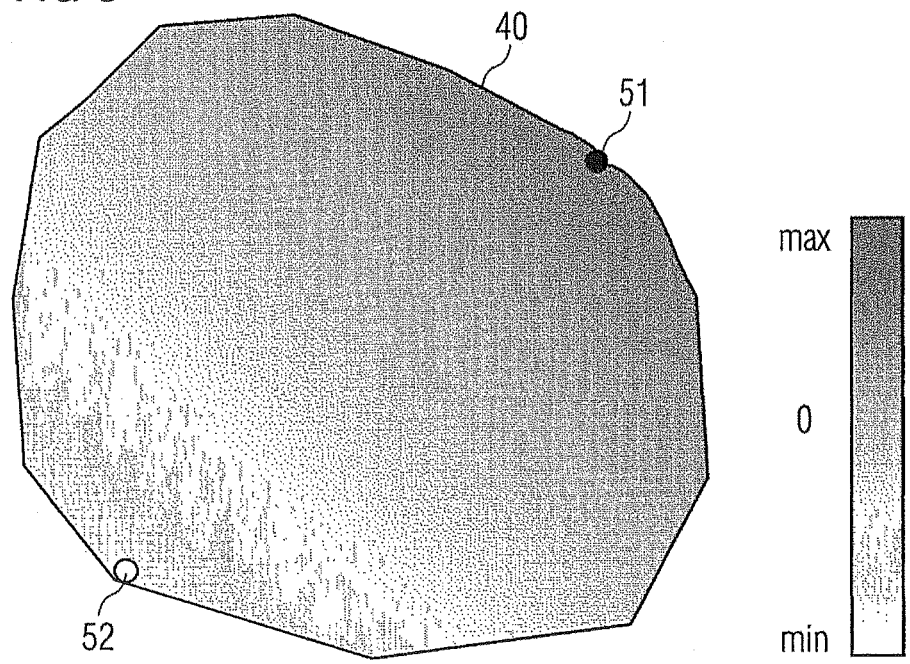
FIG. 5 shows the segment from FIG. 4 with two seed points for a random walker segmentation algorithm.

By way of example, pixels within the segment that have a maximal or minimal correction factor can be used as seed points. FIG. 4 shows, in an example fashion, a segment 40 that has a correction factor variance that exceeds the predetermined threshold. In FIG. 4, a grayscale value of a pixel corresponds to a correction factor. As illustrated in FIG. 5, a pixel 51 with a maximal correction factor and a pixel 52 with a minimal correction factor are used as seed points for the further segmentation of this segment 40. After carrying out the random walker algorithm, this results in two new partial segments 61 and 62, as illustrated in FIG. 6.

As an alternative to the random walker method, use can for example also be made of a graph-cut method (Yuri Boykov, Marie-Pierre Jolly: Interactive Organ Segmentation Using Graph Cuts, Medical Image Computing and Computer-Assisted Intervention, MICCAI 2000: 276-286, the entire contents of which are hereby incorporated herein by reference), which is based on the graph given by the segmentation of the image. The weightings in the graph can be calculated on the basis of the correction factors only or can additionally take into account the magnetic resonance image acquired in step 21, which was used for the original initial segmentation.

Neighboring segments with similar attenuation coefficients are also merged in step 28 if the total number of segments exceeds a predetermined threshold. Then the method is continued iteratively with step 23, wherein, however, there is no need for renewed raw PET data acquisition (step 24); rather, the previously acquired raw PET data is used with the new segmentation in order to calculate the emission image.

This method gradually refines and improves the segmentation for the μ-map and the attenuation coefficients of the individual segments, even if the initial segmentation was qualitatively rough and insufficient.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

List of Reference Signs
1 Positron emission tomography system
2 Tomography scanner
3 Patient couch
4 Control unit
5 Image-calculation unit 6 Examination object, patient
20 Method
21-28 Step
40 Segment
51, 52 Seed point
61, 62 Partial segment

What is claimed is:

1. A method for determining radiation attenuation by an examination object in a positron emission tomography scanner, the method comprising:
fixing an initial segmentation of the examination object, an attenuation coefficient being assigned to each segment of the segmentation and each segment including one or more pixels of the examination object;
automatically acquiring raw radiation data about the examination object with the aid of the positron emission tomography scanner, a positron emission source being arranged in the positron emission tomography scanner;
automatically determining a correction factor for each of the one or more pixels of each segment with the aid of an optimization method, a probability of the acquired raw radiation data being optimized by taking into account the segmentation and the attenuation coefficients assigned to the segments;
automatically determining a statistical parameter of the correction factors for each segment, wherein the statistical parameter of a segment is determined by the correction factors that are assigned to the one or more pixels of each segment;
automatically correcting the segmentation by subdividing each respective segment as a function of the statistical parameter determined for the respective segment; and
automatically correcting the attenuation coefficients assigned to the segments as a function of the correction factors assigned to the respective segment.

2. The method as claimed in claim 1, wherein the initial segmentation is fixed on the basis of magnetic resonance data, acquired from the examination object and automatically segmented.

3. The method as claimed in claim 2, wherein the attenuation coefficient for each segment of the initial segmentation is assigned as a function of a model.

4. The method as claimed in claim 2, wherein the method steps are carried out iteratively, starting with automatically determining a correction factor.

5. The method as claimed in claim 1, wherein the attenuation coefficient for each segment of the initial segmentation is assigned as a function of a model.

6. The method as claimed in claim 1, wherein the determining of the statistical parameter of the correction factors for each segment comprises determining a variance of the correction factors for each segment.

7. The method as claimed in claim 1, wherein the subdividing of a segment comprises an application of a random walker segmentation method.

8. The method as claimed in claim 7, wherein the pixel with a maximal correction factor and the pixel with a minimal correction factor are used as seed points for the segmentation method in the segment to be subdivided.

9. The method as claimed in claim 1, wherein the subdividing of a segment comprises an application of a graph-cut segmentation method.

10. The method as claimed in claim 9, wherein the pixel with a maximal correction factor and the pixel with a minimal correction factor are used as seed points for the segmentation method in the segment to be subdivided.

11. The method as claimed in claim 1, further comprising: automatically correcting the segmentation by merging neighboring segments as a function of the attenuation coefficients assigned to the segments.

12. The method as claimed in claim 1, wherein the method steps are carried out iteratively, starting with automatically determining a correction factor.

13. A non-transitory computer program product, directly loadable into a storage medium of a programmable control unit of a positron emission tomography system, including program segments for executing all steps of the method as claimed in claim 1, when the program is executed in the control unit.

14. A non-transitory electronically readable data medium with electronically readable control information stored thereon, embodied such that when the data medium is used in a control unit of a positron emission tomography system, said control information carries out the method as claimed in claim 1.

15. A tangible computer readable medium including program segments for, when executed on a computer device, causing the computer device to implement the method of claim 1.

16. A positron emission tomography system, comprising:
a positron emission tomography scanner, including a positron emission detector to detect radiation emitted by an examination object arranged in the positron emission tomography scanner;
a control unit to actuate the positron emission detector and to receive raw radiation data; and
an image-calculation unit to reconstruct image data from the raw radiation data,
wherein the positron emission tomography system is embodied
to fix an initial segmentation of the examination object, radiation attenuation being assigned to each segment of the segmentation and each segment comprising one or more pixels of the examination object,
to acquire automatically raw radiation data about the examination object with the aid of the positron emission tomography scanner, including a positron emission source arranged in the positron emission tomography scanner,
to determine automatically a correction factor for each pixel with the aid of an optimization method, a probability of the acquired raw radiation data being optimized by taking into account the segmentation and the attenuation coefficients assigned to the segments,
to determine automatically a statistical parameter of the correction factors for each segment, the statistical parameter of a segment being determined by the correction factors assigned to the one or more pixels of each segment,
to correct automatically the segmentation by subdividing each respective segment as a function of the statistical parameter determined for the respective segment,
to determine automatically a segment correction factor for each segment from the correction factors assigned to the respective segment, and
to correct automatically the attenuation coefficients assigned to the segments as a function of the segment correction factors.

17. The positron emission tomography system as claimed in claim 16, wherein the initial segmentation is fixed on the basis of magnetic resonance data, acquired from the examination object and automatically segmented.

* * * * *